United States Patent [19]
Sipos et al.

[11] 4,361,547
[45] Nov. 30, 1982

[54] SULFONATED AROMATIC FORMALDEHYDE CONDENSATION POLYMERS AS DENTAL PLAQUE BARRIERS

[75] Inventors: Tibor Sipos, Lebanon; Robert J. Gander, Whitehouse; Carl J. Buck, Berkeley Heights, all of N.J.

[73] Assignee: Johnson & Johnson Products, Inc., New Brunswick, N.J.

[21] Appl. No.: 172,490

[22] Filed: Jul. 25, 1980

[51] Int. Cl.³ .................. A61K 7/16; A61K 7/22; A61K 31/315; A61K 31/205
[52] U.S. Cl. ..................................... 424/56; 424/54; 424/82; 424/289; 424/316; 424/317; 528/230
[58] Field of Search ................................. 424/48–52, 424/, 78, 315; 260/505 R, 512; 528/230

[56] References Cited

U.S. PATENT DOCUMENTS 3,320,212  5/1967  Shen et al. ............................ 424/56
3,919,429  11/1975  Grossmann et al. .................. 424/78

FOREIGN PATENT DOCUMENTS 1960812  4/1969  Fed. Rep. of Germany ...... 260/512
2444785  4/1976  Fed. Rep. of Germany ...... 424/315
1507772  4/1978  United Kingdom .

Primary Examiner—Douglas W. Robinson

[57] ABSTRACT

Compositions and methods for preventing the attachment of dental plaque to the surfaces of the teeth of mammals comprise certain sulfonated aromatic formaldehyde condensation polymers and the pharmaceutically acceptable salts thereof in a pharmaceutically acceptable vehicle, and the periodic application thereof to teeth.

8 Claims, No Drawings

SULFONATED AROMATIC FORMALDEHYDE CONDENSATION POLYMERS AS DENTAL PLAQUE BARRIERS

TECHNICAL FIELD

This invention relates to oral hygiene compositions and methods using such compositions to prevent attachment of bacteria to teeth. More particularly, it relates to certain sulfonated polymeric materials that have been found useful in inhibiting the agglutination of oral microbes on teeth.

BACKGROUND ART

The prevention of the deposition of dental plaque on teeth is a highly desired result. Dental plaque results when cariogenic bacteria aggregate in colonies on the surface of teeth and form a tenacious deposit thereon. The presence of plaque on teeth is believed to be a precursor to development of dental caries and periodontal disease.

While many attempts have been made to control the effects of cariogenic bacteria and the dental plaque they produce, for example, fluoride, flossing, brushing, etc., treatments, these are typically directed to either counteracting the secondary effects of plaque on the teeth and gums, or to the removal of plaque that is already formed on and adhering to the teeth and surrounding tissue. Such treatments are not, however, entirely successful, and must be supplemented with periodic treatment by dental professionals. To date, there is no commercially feasible home treatment method for preventing the formation of plaque or its adhesion to teeth.

THE INVENTION

Certain hydrophilic sulfonic acid and sulfonic acid salt derivatives of certain aromatic formaldehyde condensation polymers have been synthesized. These polymers inhibit the deposition of dental plaque onto human teeth. These hydrophilic polymeric sulfonates have good film forming characteristics and, accordingly, are applied to teeth from various dentifrice formulations, mouth rinses, or other oral hygiene procedures. The anionic sulfonate polymers are substantially soluble in water or water/organic solvent vehicles, primarily because of the relatively high degree of sulfonation achieved during preparation of these derivatives. While the mechanism of action of the hydrophilic polymeric films in retarding plaque deposition is not known with absolute certainty, it is presumed that the films of anionically-charged polymers deposited on teeth effect a mutual repulsion between the negatively charged polymer film and the negatively charged microorganisms in oral fluids responsible for plaque generation. For example, when powdered human dental enamel is dispersed in the aqueous media containing salts of the polymeric sulfonates, a substantially negative surface charge is imparted to the enamel particles, as determined by zeta potential measurements. The sulfonated polymers of this invention are especially effective as components of dentifrices and other oral hygiene preparations in reducing dental plaque deposition on teeth.

The hydrophilic, polymeric sulfonates found useful for dental plaque control in accordance with the present invention are essentially sulfonated derivatives of formaldehyde condensation polymers of certain aromatic compounds wherein the repeating unit of the polymer is selected from the group consisting of structure (A), structure (A), 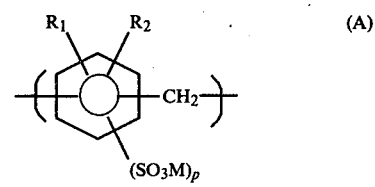

structure (B), 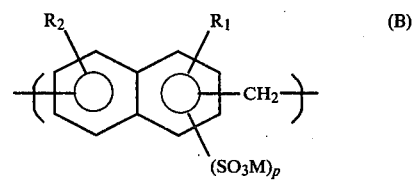

structure (C), 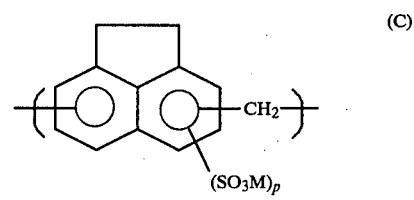

structure (D), 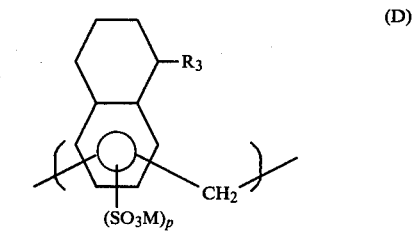

and structure (E), 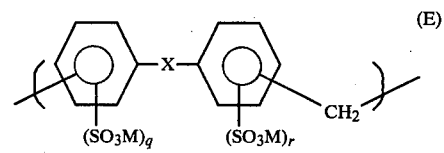

wherein $R_1$ and $R_2$ are each independently selected from the group consisting of hydrogen, linear or branched alkyl of up to 20 carbon atoms, alkoxy of 1–20 carbon atoms, fluorine, chlorine, and bromine, provided, however, that in structure (B) $R_1$ and $R_2$ cannot both be hydrogen; $R_3$ is hydrogen or an alkoxy group of up to 20 carbons; X is a linkage selected from the group consisting of a direct covalent bond between the aromatic rings, a lower alkylene of 1 to 5 carbon atoms, a lower alkylidene having 2 to 5 carbon atoms, oxygen, sulfur, and $O(CH_2)_nO$, where n is an integer from 2 to 20; p is from about 0.4 to about 1.2, (preferably about 1), the sum of q and r is between about 0.8 and about 2.4 (preferably from about 1 to about 2); and M is selected from the group consisting of lithium, sodium, potassium, calcium, magnesium, zinc, aluminum, hydrogen, ammonium and substituted ammonium ions derived from pharmaceutically acceptable organic amines. The zinc salts are particularly preferred. In general, the metal and ammonium salts are preferred over the free sulfonic acid derivatives because of their higher water solubility and lower degree of acidity (closer to neutrality), thereby flavoring their use in oral hygiene formulations for dental plaque control.

The formaldehyde polymers that are sulfonated to form the plaque barriers of this invention are preferably prepared by the acid catalyzed condensation of aqueous 37% formaldehyde or paraformaldehyde with selected aromatic compounds under standard conditions reported in the literature and reviewed extensively in the text by J. F. Walker, "Formaldehyde", R. E. Krieger Publishing Co., Third Edition, 1975. By selecting aromatic compounds of varied structure, condensation reactions with formaldehyde can afford a wide variety of aromatic/formaldehyde polymers, having generalized structure (I), wherein the unsulfonated aromatic moiety, Ar, corresponds to the aromatic structures in the repeating units of structures (A) through (E) of the sulfonated polymers defined above.

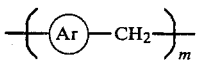 (I)

Typical examples of aromatic compounds which can be utilized for preparation of the formaldehyde polymers of general structure (I) are toluene, xylene, ethylbenzene, propylbenzene, isopropylbenzene, butylbenzene, tertiarybutylbenzene, octylbenzene, nonylbenzene, dodecylbenzene, octadecylbenzene, anisole, m-chloroanisole, diphenyl, diphenylmethane, 2,2-diphenylpropane, 1,2-diphenyl ethane (bibenzyl), 1,5-diphenylpentane, diphenyl ether, diphenyl sulfide, 2,6-dimethylnaphthalene, nonylnaphthalene, 1-chloronaphthalene; 1,2,3,4-tetrahydronaphthalene (tetralin); 1-methoxy-1,2,3,4-tetrahydronaphthalene; 1-dodecyloxy-1,2,3,4-tetrahydronaphthalene; acenaphthalene; 1,2-bis(phenoxy) ethane; 1,6-bis(phenoxy)hexane; and 1,12-bis(phenoxy)dodecane.

As indicated in structures A–E, the exact position or orientation of the methylene (—CH$_2$—) linkages on the aromatic rings is not known and is generally recognized as being complex and varied. It is well understood that some of the formaldehyde linkages may not be solely of the —CH$_2$— type but can also involve some extended units, such as CH$_2$OCH$_2$ and CH$_2$(OCH$_2$)$_n$OCH$_2$, or other possibilities (cf. Walker, supra). However, despite these uncertainties, NMR data on the unsulfonated precursors as well as the sulfonated formaldehyde polymers of this invention indicated that the formaldehyde linkages consist essentially of the methylene linkage depicted in structures A–E. The molecular weights of the unsulfonated polymers were generally in the 2000–5000 molecular weight range, as established by viscosity-average and weight-average molecular weight (light scattering) measurements.

The formaldehyde polymers are prepared by heating approximately equimolar quantities of formaldehyde and the selected aromatic compound in an inert solvent, in the presence of an acid catalyst such as sulfuric acid, p-toluenesulfonic acid, methanesulfonic acid, or perchloric acid, for several hours. Depending on the nature of the formaldehyde polymer, the latter precipitates from the reaction mixture either directly on cooling to room temperature or upon quenching in water. The preferred solvent for the reaction is acetic acid, a solvent known to favor formation of polymers having oxygen-free linkages (Walker, supra, p. 439), such as those represented by structure (I).

The sulfonated formaldehyde polymers of this invention have a molecular weight of about 500 to 10,000, preferably about 2,000 to 5,000. They are substantially soluble in water or mixed solvents comprising water and an organic solvent miscible therewith (generally at least 1% w/w). The degree of sulfonation (D.S.), defined herein as the average number of sulfonate or sulfonic acid groups per repeat unit of the polymeric structure, is an important variable which has a significant effect on the extent of dental plaque deposition.

Preferred sulfonation agents for preparing the sulfonated polymeric barriers of this invention are anhydrous sulfur trioxide, triethyl phosphate (TEP) complexes of sulfur trioxide, and chlorosulfonic acid. Due to the high reactivity of sulfur trioxide and its potent dehydration properties, sulfonation reactions with sulfur trioxide sometimes result in formation of highly insoluble polymer dispersions due to crosslinking caused by inter-polymer chain sulfone formation. In these situations, it is found preferable to moderate the sulfonation reactivity by utilization of the sulfur trioxide complexes with triethyl phosphate (TEP), which minimize or essentially eliminate formation of crosslinked by-products [cf. A. F. Turbak, Ind. Eng. Chem., Prod. R & D, 1, 275(1962); U.S. Pat. No. 3,072,619 (Jan. 8, 1963); A. F. Turbak and A. Noshay, U.S. Pat. No. 3,206,492 (Sept. 14, 1965); N. H. Canter, U.S. Pat. No. 3,642,728 (Feb. 15, 1972); A. Noshay and L. M. Robeson, J. Applied Polymer Science, 20, 1885 (1976)]. In some instances where it is difficult to effect sulfonation under milder conditions with the complexes, sulfonation with sulfur trioxide (alone) or chlorosulfonic acid is more effective.

Sulfonations are effected in solvents such as methylene chloride, 1,2-dichloroethane, and chloroform, since these are generally good solvents for the starting aromatic polymer and poor solvents for the sulfonated polymer. In those instances where the product is soluble in the reaction medium and does not precipitate, the sulfonated polymer is isolated by removing the solvent and converted to well-defined solids by either trituration or slurrying with an appropriate non-solvent.

Temperature control of the sulfonation reaction with sulfur trioxide and its complexes with TEP is not very critical. Acceptable results are obtained over a temperature range of −20° C. to +40° C. range. Sulfonations are generally effected at ambient room temperatures, since the sulfonation exotherm is very mild and rarely results in temperature increases beyond 35° C.

Typical impurities in the sulfonated polymer are small amounts of unreacted polymer, excess sulfonation agent (as sulfuric acid), and residual triethyl phosphate which are occluded in the solid polymer. Substantial purification can be effected by slurrying the polymeric sulfonic acid derivatives in non-solvents therefor, such as the halocarbons. Removal of the free sulfuric acid is difficult, since it complexes strongly with the polymeric product. Diethyl ether is an exceptionally good complexing agent for sulfuric acid and effectively removed this contaminant when freshly isolated polymeric solids are slurried in the ether and filtered. Other effective additives for sulfuric acid removal are halocarbon solvent blends with diethyl ether and other oxygenated solvents, such as ethyl acetate and acetone. The sulfuric acid, if not removed, results in contamination of the metal salts with, e.g. sodium sulfate, in the case where the sodium sulfonate polymer is produced.

The preferred process for purification of the sulfonated polymers, particularly highly water soluble types, is by dialysis in membrane tubes or hollow fiber dialyzing units having a molecular weight cut-off well below the molecular weight of the polymer. Dialysis removes all of the low molecular impurities, triethyl phosphate, and inorganic salts. High purity polymers are isolated as solids by freeze-drying or spray drying the dialyzed polymer solution.

The D.S. of the sulfonated polymers can be varied by adjusting the molar ratio of sulfonating agent to polymer. In preparing the sulfonated polymers of this invention, the exact position of sulfonation on the aromatic rings is not known with certainty, nor is it considered important in the practice of this invention. The D.S. of the formaldehyde polymers, either as their sulfonic acid or sulonate salt derivatives, can be determined by any of several methods: (a) NMR analysis, (b) elemental analysis for sulfur to carbon ratio determination, (c) direct titration of the sulfonic acid derivative with standard sodium hydroxide to obtain the milliequivalents of sulfonic acid groups per gram of sample, a value approximately equivalent to the ion-exchange capacity of the sulfonated polymer, or (d) atomic absorption assay for the metal content of carefully purified samples of the sulfonated salts.

The alkali metal salts of the sulfonated polymers are conveniently prepared by neutralization of a water or alcohol solution of the polymeric sulfonic acid derivative with alkali metal hydroxide solutions to the potentiometric endpoint. The salts are recovered by filtration, solvent stripping, or freeze drying, depending on the type of solvent used and whether the salt precipitates directly from the solvent media. Alternatively, sulfonate salts can be prepared by addition of at least stoichiometric quantities of an alkali metal oxide, carbonate, acetate, chloride, nitrate, or sulfate to the sulfonic acid derivative. The salts either precipitate directly and are collected, or they are isolated after solvent stripping. Purification of the sulfonate salt by dialysis is the preferred procedure for the more highly water soluble salts.

Multivalent metal salts, such as calcium, magnesium, zinc, and aluminum salts, of the sulfonated polymers are prepared by methods similar to those described above. In an alternate procedure, multivalent metal salts can be prepared by an ion-exchange reaction between the multivalent ion and either the free sulfonic acid or an alkali metal sulfonate derivative of the polymer. The neutralization and other salt forming reactions described above are essentially ion-exchange reactions, as typified by the following equations, where P represents the polymer chain:

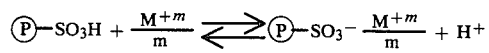

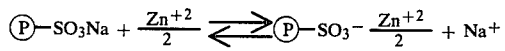

Ammonium salts of the sulfonic acid polymer can be prepared by direct addition of ammonia or a primary, secondary, or tertiary organic amine.

For testing the sulfonated formaldehyde polymers of this invention, the in vitro test procedure we have employed begins with growth of plaque in small jars containing sterilized trypticase media that has been supplemented with sucrose. Typically, ten jars are individually inoculated with 0.5 ml of unpooled freshly collected human plaque from 10 subjects. In a control series, a presterilized glass slide or an extracted human tooth is inserted into each jar. In the test series, the tooth or glass slide is pretreated with a 1% solution of the test compound (dissolved in water or other vehicle), allowed to dry in order to deposit a thin film of the compound on the surface, and the glass slide or tooth placed in the growth media. The jars are incubated under anaerobic conditions for two days at 37° C. The tooth or glass slide is removed, air dried, and stained with 0.15% FD&C #3 red dye solution to reveal the accumulated plaque deposits. The tooth or glass slide is scored for plaque density of a 0 to 5 scale. Plaque barrier activity is reported as the % of average plaque reduction, as compared to appropriate controls for ten subjects.

The effect of the degree of sulfonation (D.S.) of the formaldehyde polymers of this invention on their plaque barrier properties is shown in Table 1, which illustrates the necessity of achieving a certain minimal D.S. value in order to develop adequate plaque barrier properties. For example, acceptable reductions in the deposition of plaque are obtained when the D.S. of sulfonated polymers of structures (A) through (D) is at least about 0.4. In sulfonated polymers of structure (E), where there are two phenyl rings in each repeat unit, the D.S. should average at least about 0.8 per repeat unit or about 0.4 per phenyl ring.

TABLE 1

| Plague Barrier Properties of Sulfonated Aromatic Formaldehyde Polymers | | | |
|---|---|---|---|
| Polymer Prepared From | M | D.S. | % Plaque Reduction |
| CH₃—⌬—CH₃ (2,6) | Na | 0.9 | 48 |
| CH₃—⌬—CH₃ (para) | Na | 0.6 | 34 |
| | Na | 1.1 | 22 |
| Cl—⌬—OCH₃ | Na | 0.7 | 54 |
| Cl-naphthalene | Na | 0.8 | 70 |
| naphthalene | Na | 0.5 | 67 |
| acenaphthalene | Na | 1.2 | 38 |
| ⌬—(CH₃)₈CH₃ | Na | 0.8 | 81 |
| ⌬—CH₂CH₂—⌬ | Na | 1.0 | 25 |
| | Na | 1.4 | 40–54 |
| ⌬—CH₂—⌬ | Na | 2.0 | 73 |
| ⌬—S—⌬ | Na | 1.0 | 48 |
| ⌬—O(CH₂)₁₂O—⌬ | Na | 1.6 | 65 |

EXAMPLE 1

Formaldehyde Polymer of 1-Phenylnonane

A mixture of 10.2 g (0.05 mole) 1-phenylnonane, 60 ml. glacial acetic acid, and 2.7 ml. (0.05 mole) 96% sulfuric acid was stirred and heated to 108° C. A solution of 4.1 g (0.05 mole) 37% formaldehyde in 20 ml. acetic acid and was added over 30 minutes at 108°–114° C. The clear, orange-brown solution was maintained at reflux for 18.5 hours and the reaction contents stripped free of acetic acid by heating under reduced pressure. The residual syrup was dissolved in 150 ml. methylene chloride, extracted with water, 1 N sodium hydroxide, and water; dried over magnesium sulfate, filtered, and solvent stripped to give 9.6 g of the formaldehyde polymer. The latter was soluble in solvents such as hexane, acetone, and methylene chloride; slightly soluble in ethanol; and insoluble in methanol.

EXAMPLE 2

Sulfonation of 1-Phenylnonane/Formaldehyde Polymer

A solution of 5.2 g (0.024 mole) of the 1-phenylnonane/formaldehyde polymer (Example 1) in 52 ml. methylene chloride was added over 45 minutes at 23°–28° C. to a stirred solution of 3.8 g (0.048 mole) liquid sulfur trioxide dissolved in 36 ml. methylene chloride. After stirring another 100 minutes at 26°–28° C., the solution phase was decanted from the gum which was triturated several times with hexane. The hexane-insolubles were dissolved in 200 ml. chloroform and extracted with water containing some methanol to break the emulsion which formed. Removal of the chloroform gave 1.2 g of the sulfonic acid derivative of the polymer which was dissolved in 50 ml. methanol and neutralized from pH 1.5 to the potentiometric endpoint with 5.1 ml. methanolic 0.512 N sodium hydroxide. The solvent was removed, and the crude sodium sulfonate derivative was dissolved in water and the solution extracted with hexane to remove non-polar impurities. The aqueous phase was concentrated to give 0.7 g of the sodium sulfonate derivative, a brown powder showing a D.S. of 0.8 via NMR analysis.

EXAMPLE 3

Formaldehyde Polymer of 1,12-Bis(phenoxy)dodecane

A mixture consisting of 17.7 g 1,12-bis(phenoxy)dodecane, 90 ml. glacial acetic acid, and 0.95 g p-toluenesulfonic acid monohydrate was heated to 100° C. and 4.1 g 37% formaldehyde, dissolved in 10 ml. acetic acid, added over 20 minutes at a temperature of 100°–110° C. Heating was continued for 6 hours, cooled to room temperature, and the mixtured diluted with 175 ml. water. The gummy polymer was extracted into chloroform, and the combined extracts were washed with water, 5% sodium hydroxide, water, and dried over magnesium sulfate. Filtration and solvent removal gave 18.1 g of the formaldehyde polymer as a pale orange, viscous liquid which hardened on standing.

EXAMPLE 4

Sulfonation of 1,12-Bis(phenoxy)dodecane/Formaldehyde Polymer

With stirring, a solution of 1.76 g (0.022 mole) liquid sulfur trioxide in 9 ml. methylene chloride was added over 30 minutes at 8°–11° C. to a solution of 3.7 g of the formaldehyde polymer, from Example 3, in 37 ml. methylene chloride. The reaction mixture was allowed to warm to 21° C. over one hour, and the red solids were filtered, washed with 4×30 ml. methylene chloride and 4×30 ml. ether. The solids were slurried in 100 ml. methanol, the gelatinous, solvent swollen solids filtered, re-slurried in 100 ml. methanol, filtered, washed with hexane, and dried to give 4.0 g of crosslinked polymer. The methanolic filtrates obtained from washing of the crosslinked polymer fraction gave, after solvent removal, 1.6 g of the sulfonic acid derivative of the formaldehyde polymer. Dissolution in 32 ml. methanol, neutralization with sodium hydroxide to pH 8.5, filtration from a small amount of insolubles, and solvent removal gave 1.2 g of the polymeric sodium sulfonate derivative. The D.S. was 1.6, as determined by NMR assay.

EXAMPLE 5

Formaldehyde Polymer of 1-Chloronaphthalene

A solution of 32.5 g (0.200 mole) 1-chloronaphthalene, 165 ml. glacial acetic acid, and 11 ml. (0.200 mole) 96% sulfonic acid was maintained at reflux during addition of 16 ml. (0.200 mole) 37% formaldehyde over 15 minutes. After an additional 22 hours at reflux, the reaction mixture was cooled to room temperature and the supernatant solution decanted from the yellow gum which separated. The gum was dissolved in 200 ml. toluene, and the solution was extracted with 1 N sodium hydroxide, water, and saturated sodium chloride solution. After drying over magnesium sulfate, the toluene extract was solvent stripped to give 33.2 g of the formaldehyde polymer, a clear, orange gum.

EXAMPLE 6

Sulfonation of 1-Chloronaphthalene/Formaldehyde Polymer

A flask was charged with 25 ml. methylene chloride and fitted with two addition funnels, one containing a solution of 5.0 g 1-chloronaphthalene/formaldehyde polymer (Example 5) in 25 ml. methylene chloride and the other funnel containing 1.5 ml. liquid sulfur trioxide dissolved in 24 ml. methylene chloride. With stirring, the two solutions were added simultaneously over 14 minutes at 27°–30° C. to the solvent in the flask. The reaction mixture was stirred another one hour at 27°–30° C. and the solution phase decanted from the polymeric gum. The latter was triturated with 2×50 ml. methylene chloride and 3×50 ml. ether. On drying in vacuo at 60° C., there was obtained 1.6 g of the polymeric sulfonic acid derivative.

Neutralization of a solution of 1.5800 g of the sulfonic acid derivative in 30 ml. methanol, pH 1.6, with 10.5 ml. 0.492 N sodium hydroxide in methanol gave, after solvent removal, 1.5 g of the sodium sulfonate derivative of the polymer as pale orange solids. Based on the titer, the D.S. was 0.8.

EXAMPLE 7

Formaldehyde Polymer of 1,2,3,4-Tetrahydronaphthalene (Tetralin)

A solution of 26.4 g (0.200 mole) tetralin, 130 ml. glacial acetic acid, and 11 ml. (0.200 mole) 96% sulfonic acid was maintained at about 100°–115° C. during addition over 40 minutes of a solution of 16.2 g (0.200 mole) 37% formaldehyde in 40 ml. acetic acid. After heating another 4 hours, the solution was cooled to room temperature, during which time the gum present converted to finely suspended solids. The solids were dissolved in 150 ml. chloroform and the solution added slowly with stirring to 750 ml. methanol to precipitate the formaldehyde polymer which was filtered, washed with methanol, and dried. The yield was 24.7 g.

EXAMPLE 8

Sulfonation of Tetralin/Formaldehyde Polymer

A solution of 7.2 g (0.05 mole repeat unit) of the tetralin/formaldehyde polymer (Example 7) in 72 ml. methylene chloride was cooled to 13° C. and a solution of 5.0 g (0.063 mole) liquid sulfur trioxide in 26 ml. methylene chloride added over 30 minutes at 11° to 13° C. The reaction contents were allowed to warm to room temperature over about one hour and the solution phase decanted from the red gum deposit. The gum was triturated with 5×50 ml. methylene chloride. On trituration with 100 ml. ether, the gum converted to brown solids which were filtered, washed with ether, and dried to give 6.4 g of the polymeric sulfonic acid derivative.

A solution of 3.8556 g of the polymeric sulfonic acid in 76 ml. methanol, pH 1.6, was neutralized with 19.8 ml. 0.512 N methanolic sodium hydroxide. Based on the titer, the D.S. was 0.5. Solvent stripping the neutralized solution gave 4.2 g of the polymeric sodium sulfonate derivative.

The plaque barrier oral compositions of this invention may comprise any conventional pharmaceutically acceptable oral hygiene formulation that contains (and is compatible with) an effective amount of a plaque barrier agent as defined herein. Such formulations include, for example, mouthwashes, rinses, irrigating solutions, abrasive and nonabrasive gel dentifrices, denture cleansers, coated dental floss and interdental stimulator coatings, chewing gums, lozenges, breath fresheners, foams and sprays.

The plaque barrier agents may be present in these formulations in effective concentrations generally in the range of from about 0.05 weight percent to as much as 30 weight percent or the limit of compatibility with the vehicle. However, no advantage will be derived from concentrations in excess of about 20 weight percent. A prefered concentration range for the plaque barrier agents in the formulations of the invention is from about 0.5 to about 10 weight percent. A more preferred range is from about 2 to about 8 percent by weight, about 5% being the presently most preferred concentration in a nonabrasive gel vehicle.

The pH of these plaque barrier preparations should be between pH 5.0 and 10.0, preferably between pH 5.0 and 8.0, more preferably between about pH 6.0 and 7.5. Lower pH than 5.0 is undesirable because of the possible enhancement of enamel demineralization.

Suitable conventional pharmaceutically acceptable vehicles that can be employed with the plaque barrier agents to prepare the barrier compositions of this invention may comprise water, ethanol; such humectants as polypropylene glycol, glycerol and sorbitol; such gelling agents as cellulose derivatives, for example, Methocel, carboxymethylcellulose (CMC 7MF) and Klucel HF, polyoxypropylene/polyoxyethylene block copolymers, for example, Pluronic F-127, Pluronic F-108, Pluronic P-103, Pluronic P-104, Pluronic P-105, and Pluronic P-123, colloidial magnesium aluminosilicate complexes such as Veegum, and mucoprotein thickening agents such as Carbopol 934; gel stabilizers such as the silicon dioxides, for example, Cab-O-Sil M5, and polyvinylpyrrolidone; sweeteners such as sodium saccharin; preservatives such as citric acid, sodium benzoate, cetylpyridinium chloride, potassium sorbate, methyl and ethyl parabens; detergents such as sodium lauryl sulfate, sodium cocomonoglyceride sulfonate, sodium lauryl sarcosinate and polyoxyethylene isohexadecyl ether (Arlasolve 200) and approved colors and flavors.

The following specific examples will serve further to illustrate the plaque barrier compositions of this invention.

EXAMPLE A

| Mouthwash Solution | |
|---|---|
| Barrier Agent | 0.5–2.0% w/w |
| Glycerol (humectant) | 6.0 |
| Pluronic F-108 | 1.0 |
| Sodium saccharin (sweetener) | 0.3 |
| Deionized Water | q.s. |
| Flavors | 1.0 |
| | 100.0 |

EXAMPLE B

| Mouthwash Solution | |
|---|---|
| Plaque Barrier Agent | 0.5–3.0% w/w |
| Ethanol, USP | 15.0 |
| Pluronic F-108 (foaming agent) | 2.0 |
| Glycerol (humectant) | 10.0 |
| Sorbitol (humectant) | 10.0 |
| Sodium saccharin (sweetener) | 0.2 |
| Deionized Water | q.s. |
| Flavors | 0.2 |
| | 100.0 |

EXAMPLE C

| Abrasive Dentifrice Gel | |
|---|---|
| Plaque Barrier Agent | 2.0–10.0% w/w |
| Fumed Silica (abrasive) | 55.0 |
| Sodium Lauryl Sulfate (detergent) | 1.5 |
| Glycerol (humectant) | 10.0 |
| Carboxymethylcellulose (gelling agent) | 2.0 |
| Sodium saccharin (sweetener) | 0.2 |
| Sorbitol (humectant) | 10.0 |
| Flavors | 1.0 |
| Deionized Water | q.s. |
| Preservative | 0.05 |
| | 100.0 |

EXAMPLE D

| Chewing Gum | |
|---|---|
| Plaque Barrier Agent | 1.0–11.0% w/w |
| Gum Base | 21.3 |
| Sugar | 48.5–58.5 |
| Corn Syrup (Baume 45) | 18.2 |
| Flavors | 1.0 |
| | 100.0 |

EXAMPLE E

| Nonabrasive Gel Dentifrice | |
| --- | --- |
| Plaque Barrier Agent | 0.05–30.0% w/w |
| Sorbistat (preservative) | 0.15 |
| Deionized Water | q.s. |
| Silicon Dioxide (gel stabilizer) | 1.0 |
| Pluronic F-127 (gelling agent) | 20.0 |
| Sodium Saccharin | 0.2 |
| Flavors | 1.5 |
| | 100.0 |

EXAMPLE F

The following formulation illustrates a presently preferred nonabrasive gel composition containing a barrier agent in accordance with the present invention.

| Ingredients | % w/w |
| --- | --- |
| Distilled Water | q.s. |
| Sodium Saccharin (sweetener) | 0.20 |
| Sodium Benzoate (preservative) | 0.30 |
| FD&C Blue #1 (0.1% aq. soln.) | 0.27 |
| D&C Yellow #10 (0.5% aq. soln.) | 0.50 |
| Gelling agent | 18.00 |
| Glycerol (Humectant) | 20.00 |
| Cab-O-Sil M5 (Silicon Dioxide) | 1.00 |
| Plaque Barrier Agent | 5.00 (dry basis) |
| Flavor | 0.80 |
| | 100.0 |

While the details of preparing all of the above formulations are well within the skill of the art, a suggested procedure for preparing the gel formulation of this example will be described for completeness.

In a first container the water, sodium saccharin, sodium benzoate and dyes are mixed. Then the container is put into an ice bath. When the temperature reaches 6° C., the gelling agent is added and the contents mixed slowly until the gelling agent is dissolved. Then the solution is heated to 70° C.

Into a second container is added the glycerin. Then the Cab-O-Sil M5 is sprinkled in with mixing. Then the plaque barrier agent is added and mixing continued to a smooth paste. The paste is then heated in a water bath with mixing to a temperature of 70° C.

The contents of the first container are added to the second container and blended together until the batch is homogeneous while maintaining a 70° C. temperature. Then the flavoring is added, all mixing is stopped, and the formulation allowed to settle for approximately one hour. If necessary to remove air bubbles, overnight refrigeration may be employed.

While any pharmaceutically acceptable gelling agent that is compatible with the plaque barrier agent may be employed, a presently preferred gelling agent is Pluronic F-127.

These compositions are preferably employed from one to three times daily in a routine oral hygiene program to prevent the attachment of plaque to the teeth.

Variations can, of course, be made without departing from the spirit or scope of the invention.

We claim:

1. An oral hygiene composition comprising an effective amount for preventing deposition of dental plaque on teeth of a sulfonated condensation polymer of formaldehyde with an aromatic compound, said polymer having repeating units selected from the group consisting of structure (A), structure (A), 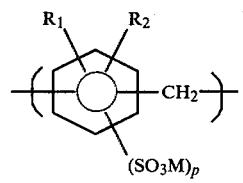

structure (B), 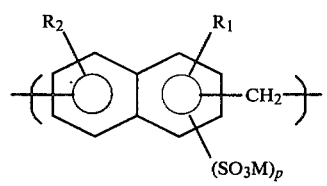

structure (C), 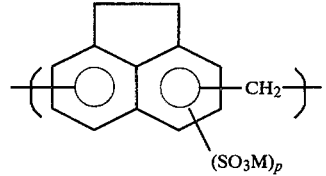

structure (D), 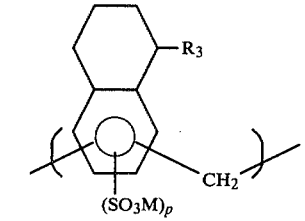

and structure (E), 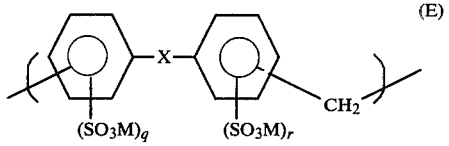

wherein $R_1$ and $R_2$ are each independently selected from the group consisting of hydrogen, linear or branched alkyl of up to 20 carbon atoms, alkoxy of 1–20 carbon atoms, fluorine, chlorine, and bromine, provided, however, that in structure (B) $R_1$ and $R_2$ cannot both be hydrogen; $R_3$ is hydrogen or an alkoxy group of up to 20 carbon atoms; X is a linkage selected from the group consisting of a direct covalent bond between the aromatic rings, a lower alkylene of 1 to 5 carbon atoms, a lower alkylidene having 2 to 5 carbon atoms, oxygen, sulfur, and $O(CH_2)_nO$, where n is an integer from 2 to 20; p is from about 0.4 to about 1.2, the sum of q and r is between about 0.8 and about 2.4 and M is selected from the group consisting of lithium, sodium, potassium, calcium, magnesium, zinc, aluminum, hydrogen, ammonium and substituted ammonium ions derived from pharmaceutically acceptable organic amines, said polymer having a molecular weight in the range of from about 500 to about 10,000, in a pharmaceutically acceptable oral hygiene vehicle compatible with said polymer.

2. The composition of claim 1 wherein M is a metal selected from the group consisting of potassium, lithium, sodium, calcium, magnesium, zinc and aluminum.

3. The composition of claim 1 wherein p is about 1.

4. The composition of claim 1 wherein the sum of q and r is between about 1 and about 2.

5. The composition of claim 1 wherein said molecular weight range is from about 2,000 to about 5,000.

6. A method of preventing deposition of dental plaque on teeth comprising periodically applying to the teeth a composition of claim 1.

7. The method of claim 6 wherein said composition is applied from about 1 to about 3 times per day.

8. The composition of claim 1 in the form of an oral hygiene formulation selected from the group consisting of mouthwashes, mouthrinses, irrigating solutions, abrasive gel dentifrices, non-abrasive gel dentifrices, denture cleansers, coated dental floss, coated interdental stimulators, chewing gums, lozenges, breath fresheners, foams and sprays.

* * * * *